United States Patent [19]

Friedrich-Fiechtl et al.

[11] Patent Number: 4,835,257

[45] Date of Patent: May 30, 1989

[54] PROCESS FOR PREPARING GAMMA GLOBULIN SUITABLE FOR INTRAVENOUS ADMINISTRATION USING PEG AND A CITRATE BUFFER

[75] Inventors: Jürgen-Dietrich Friedrich-Fiechtl, Bad Sooden-Allendorf; Bernhard Kerner, Münster; Jürgen Holzapfel, Eschwege; Martin Puschmann, Bergisch Gladbach, all of Fed. Rep. of Germany; Tokusuke Kimura, Tokyo; Fumio Kurosu, Hasuda, both of Japan

[73] Assignee: Armour Pharma GmbH, Eschwege, Fed. Rep. of Germany

[21] Appl. No.: 125,747

[22] Filed: Nov. 19, 1987

Related U.S. Application Data

[63] Continuation of Ser. No. 849,510, Apr. 21, 1986, abandoned.

[30] Foreign Application Priority Data

Jul. 7, 1984 [DE] Fed. Rep. of Germany ..... 84107985

[51] Int. Cl.$^4$ .................. A61K 39/395; C07K 3/28
[52] U.S. Cl. ................... 530/387; 424/85.8; 530/831
[58] Field of Search ............... 424/88, 85.8; 520/387, 520/831

[56] References Cited

U.S. PATENT DOCUMENTS

| | | | |
|---|---|---|---|
| 3,415,804 | 12/1968 | Polson | 530/387 X |
| 3,763,135 | 10/1973 | Shanbrom et al. | 530/387 |
| 3,790,552 | 2/1974 | Johnson et al. | 530/387 X |
| 3,808,189 | 4/1974 | Breuer | 530/387 |
| 3,869,436 | 3/1975 | Falksveden | 530/387 X |
| 4,124,576 | 11/1978 | Coval | 530/387 |
| 4,126,605 | 11/1978 | Schneider et al. | 530/387 X |
| 4,165,370 | 8/1979 | Coval | 424/85 X |
| 4,168,303 | 9/1979 | Nishida et al. | 530/387 |
| 4,276,283 | 6/1981 | Eibl et al. | 530/387 X |
| 4,371,520 | 2/1983 | Uemura et al. | 530/387 X |
| 4,379,086 | 4/1983 | Kimura et al. | 530/387 |

FOREIGN PATENT DOCUMENTS 0078331 5/1983 European Pat. Off. .
2751717 7/1978 Fed. Rep. of Germany .

OTHER PUBLICATIONS

EP, A1, 0078331 (The Green Cross), May 11, 1983, See claim 1.
DE, A1, 2751717 (M. L. Coval), Jul. 13, 1978, See claim 1.
European Search Report, Feb. 21, 1985.

Primary Examiner—Howard E. Schain
Attorney, Agent, or Firm—Wegner & Bretschneider

[57] ABSTRACT

An improved process for the preparation of gamma globulin suitable for intravenous administration comprises dissolving gamma globulin precipitated from blood or blood products in a solution, separating non-dissolved precipitate from the solution, adding polyethylene glycol to the separated solution, separating precipitate from the polyethylene glycol solution, increasing the polyethylene glycol concentration in the solution, separating precipitated purified gamma globulin from the higher concentrated polyethylene glycol solution, dissolving the purified gamma globulin in a solution suitable for intravenous administration, which process is improved by dissolving the gamma globulin precipitated from blood in a solution having a neutral pH, adding polyethylene glycol in the first step to a concentration of 4.0–5.5% by weight, and increasing the polyethylene glycol concentration in the second step to at least 9% but not more than 16% by weight, and by adding a buffer to the solution just prior to adding the polyethylene glycol in one of the two polyethylene glycol addition steps.

12 Claims, No Drawings

PROCESS FOR PREPARING GAMMA GLOBULIN SUITABLE FOR INTRAVENOUS ADMINISTRATION USING PEG AND A CITRATE BUFFER

This application is a continuation of application Ser. No. 849,510, filed Apr. 21, 1986, now abandoned.

FIELD OF THE INVENTION

This invention relates to a product containing gamma globulin suitable for intravenous administration and a process for producing the product.

BACKGROUND OF THE INVENTION

U.S. Pat. No. 4,126,605 (Schneider) described a process for obtaining a product suitable for intravenous administration from Cohn Fraction II gamma globulin. Cohn Fraction II is dissolved in a buffered aqueous solution at pH 6.7. The solution contains hydroxyethyl starch. After filtering the solution, polyethylene glycol is added to a concentration of 10%. After removal of the precipitate, additional polyethylene glycol is added to the solution to a concentration of 20%. The precipitate which results is improved unmodified gamma globulin suitable for intravenous use.

U.S. Pat. No. 4,165,370 (Coval) describes a process for obtaining a product suitable for intravenous administration from Cohn fraction II gamma globulin. Cohn fraction II is dissolved in solution having an acid pH of 4.8 to 6.5 and a low ionic strength, i.e., having a conductance of about $300-10^{-6} cm^{-1} ohm^{-1}$. After filtering the solution, polyethylene glycol, molecular weight 4,000, is added first to a 4% concentrate, then 5% concentrate. After the solution is centrifuged and any precipitate is removed, additional polyethylene glycol is added to the solution to a 12% concentration. The resulting precipitate is an immunologically active unmodiifed gamma globulin suitable for intravenous use.

In the above mentioned processes, the yields of pure gamma globulin are about 30% of the gamma globulin of the Cohn Fraction II. Modifications have been made to increase yields, but the increased yield has generally been at the expense of purity. An increased yield at constant quality of the product has not yet been possible.

It is an object of the present invention to isolate gamma globulin of high purity, suitable for intravenous use, in high yield.

SUMMARY OF THE INVENTION

An improved process for preparing gamma globulin suitable for intravenous administration comprising (a) dissolving gamma globulin precipitated from blood or blood products in a solution;

(b) separating non-dissolved precipitate from solution;

(c) adding polyethylene glycol to the separated solution;

(d) separating precipitate from the polyethylene glycol solution;

(e) increasing the polyethylene glycol concentration in the solution;

(f) separating precipitated purified gamma globulin from the higher concentration polyethylene glycol solution;

(g) dissolving the purified gamma globulin in a solution suitable for intravenous administration wherein the improvement comprises (1) the solution in which the gamma globulin is dissolved
is at a neutral pH;

(2) in the first polyethylene glycol addition step, adding the polyethylene glycol to a concentration of 4.0–5.5% by weight;

(3) in the second polyethylene glycol addition step, increasing the polyethylene glycol concentration to at least 9%, but not more than 16% by weight;

(4) adding a buffer to the solution just prior to adding the polyethylene glycol in one of the polyethylene glycol addition steps.

DETAILED DESCRIPTION OF THE INVENTION (a) Dissolving gamma globulin precipitated from blood products in solution.

The gamma globulin useful as the starting material for the product and process of the current invention is well known in the art.

A particular process for the precipitation and isolation of gamma globulin from blood is known by the name "Cohn-Method" (Cohn et al., J. Amer. Chem. Soc., Vol. 68, pp. 459–475 and Vol. 72, pp. 465–474) or "Cohn Fraction II".

This gamma globulin preparation, unsuitable for intravenous use, is dissolved in an aqueous solution at a neutral pH. The aqueous solution has a low ionic strength. The low ion concentration can be derived from salt present in the starting gamma globulin preparation or can be due to added buffer. All physiologically tolerated salts are suitable as buffers. These include phosphate, citrate and trihydroxy-ethyl-aminomethane.

The ionic concentration can be within the range of 0.001–0.015 mol/l. If buffer is added, it is preferred that the range be 0.01–0.015 mol/l.

The pH of the solution can be adjusted to $7.0 \pm 0.1$ by addition of a suitable acid or base, for example, citric acid, sodium citrate or, if needed, sodium hydroxide; citrate is preferred.

It has been found that the higher the ionic concentration, the lower the temperature of the solution should be. If no additional buffer is used, the temperature of the solution may be room temperature. If the ionic concentrate is between 0.01–0.015 mol/l, the temperature should be between 5–15° C.

The gamma globulin is dissolved in the solution in a concentration of 1–7% by weight. Preferably, the concentrate is 3.1–4.9%.

Also present in the solution may be "hdyrocolloid" such as hydroxyethyl starch, dextrose, albumin, polyalcohol and polyvinyl pyrrolidone as disclosed in U.S. Pat. No. 4,126,605.

(b) Separating non-dissolved precipitate from solution.

After the gamma globulin has been dissolved, the insoluble impurities are removed from the solution by, for example, decantation, filtration, or centrifugation.

(c) Adding polyethylene glycol to the separated solution.

To the resultant supernatant is added polyethylene glycol (PEG) having a molecular weight between 2000–6000. Preferably, the PEG will have a molecular weight average of 4000.

The PEG may be added to the supernatant in bulk, as a powder or as solution having PEG dissolved therein. PEG is added at room temperature to the separated solution to a concentration of 3–6% by weight, preferably 4.0–5.5% by weight.

It is important to add a buffer to the gamma globulin solution just prior to adding PEG in one of PEG addition steps. The buffers useful are listed above. The ionic concentration of the solution after the addition of buffer should be 0.025–0.25 mol/l.

(d) Separating precipitate form PEG solution

After the PEG is added to the 3–6% concentration, a precipitate is formed. The precipitate is removed by decantation, filtration or centrifugation.

(e) Increasing the polyethylene glycol concentration.

The concentration of PEG in the solution is increased to 9–16% by weight by the addition of PEG. The temperature of the solution at this step may be reduced to 0°–10° C., however, it may remain at room temperature.

(f) Separating precipitated purified gamma globulin.

The purified immunoglobulin which precipitates after increasing the concentration of PEG is then separated by means of gentle separation procedures, for example, decantation, filtration, or centrifugation. Preferably, the separation is by means of centrifugation.

The obtained purified gamma globulin is native, has low ACA and is suitable for use in products for intravenous administration.

(g) Dissolving the purified gamma globulin in a solution suitable for intravenous administration.

The purified gamma globulin is preferably dissolved in aqueous solution at a concentration 2–10%, preferably about 5%. The solutions may also contain buffer, e.g., citrate and/or phosphate, sugar, e.g. glucose, maltose, sucrose, and an isotonicity agent, e.g. NaCl; citrate is preferred.

Preferred are solutions containing 2–3% by weight glucose and 5–50 mmol/l sodium citrate with a pH of 7. In the process of the current invention yields are obtained of 70% or more of high quality product based on the amount of gamma globulin in the starting material. The average anti-complementary activity (ACA) of the product is approximately 10 $CH_{50}$ u/ml or less (protein concentrate of 5%).

EXAMPLE 1

Cohn-Fraction-II-Powder is dissolved in a 0.01 molar phosphate-citrate-buffer (7.00 pH, 10° C.) with careful stirring to a protein concentration of 3.5%. Hydroxyethyl starch is present in a concentration of 0.5%.

The precipitate formed is removed and the solution is clarified by layer filtrations in one filtration step. The the protein concentration is adjusted to 2.5% and the phosphate-citrate concentration is adjusted to 0.12 molar and the pH is adjusted to 7.0±0.1 by addition of a 0.5 molar phosphate-citrate-buffer (molarity related to content of phosphate/citrate). After the solution is heated to a temperature of 20° C., solid polyethylene glycol (PEG 4000 molecular weight 4000) to a concentration of 5.5% is added under careful stirring and completely dissolved.

Then the supernatant is decanted from the precipitate formed and is clarified by layer filtration.

The clarified supernatant is cooled to a temperature of 10° C. and then diluted, with stirring, with a 50% solution of PEG 4000 in a 0.03 molar phosphate-citrate-buffer at 10° C. to a PEG 4000 concentration of 14%.

The precipitate formed (paste) is collected by continuous centrifugation.

The paste is dissolved in a 20 mmolar sodium-citrate-solution (pH=7.0±0.1) and 2.5% glucose is added. The so-prepared solution shows the following characteristic values:

protein: 5.4%
pH 7.00±0.05
glucose: 2.5%±0.5%
osmolarity: 300–330 mosmol/l
ACA: 10 U/ml
HPLC: dimers+monomers: 99%

The solution is sterile filtered and placed into vials and, optionally, lyophilized.

EXAMPLE 2

Cohn-Fraction-II Powder is dissolved, at room temperature and pH of 7, in water for injection with careful stirring to a protein concentration of 5%. Hydroxyethyl starch is present in a concentration of 0.5%.

The precipitate formed is removed and the solution is clarified by layer filtration within one filtration step. Polyethylene glycol (PEG 4000), as a 40% solution, is added, under careful stirring, to a concentration of 4.0%. The precipitate is removed by depth filtration. To the clear supernatant 0.3M phosphate buffer is added to a concentration of 10% by volume and the PEG 4000 concentration is increased 10.4%.

The precipitate formed (paste) is collected by continous centrifugation.

The paste is dissolved in a 10 mM citrate/10 mM phosphate buffer (pH 7.0±0.1) additionally containing 0.9% NaCl and 2.5% glucose.

The redissolved solution had the following characteristics:

protein: 5.4%
pH 7.00±0.05
glucose: 2.5% ±0.5%
ACA: 10 U/ml
HPLC: dimers+monomers: 99%

The solution is sterile filtered, filled into bottles, and, optionally freeze-dried.

The yield of immunoglobulin based on percentage of immunoglobulin in Cohn fraction II is excess of 70%.

What is claimed is:

1. An improved process for preparing gamma globulin suitable for intravenous administration comprising
    (a) dissolving gamma globulin precipitated from blood or blood products in a solution;
    (b) separating non-dissolved precipitate from the solution;
    (c) adding polyethylene glycol to the separated solution;
    (d) separating precipitate from the polyethylene glycol solution;
    (f) separating precipitated purified gamma globulin from the higher concentrated polyethylene glycol solution;
    (g) dissolving the purified gamma globulin in a solution suitable for intravenous administration wherein the improvement comprises:
       (1) the gamma globulin precipitated from blood or blood products is dissolved in a solution having a pH 7±0.1;
       (2) in the first polyethylene glycol addition step, adding the polyethylene glycol to a concentration of 4.0–5.5% by weight;

(3) in the second polyethylene glycol addition step, increasing the polyethylene glycol concentration to at least 9%, but not more than 16% by weight;

(4) adding a 5-50 mmol/l citrate buffer (pH 7.0±0.1) buffer to the solution just prior to adding the polyethylene glycol in one of the polyethylene glycol addition steps.

2. The process of claim 1 wherein the polyethylene glycol has a molecular weight average of about 4000.

3. A process of claim 1 further comprising the improvement of in step (a) dissolving the gamma globulin in a solution having an ion concentration of 0.001 to 0.05 mol/l at a temperature not exceeding 20° C.

4. A process of claim 1 wherein hydroxyethyl starch is added to the solution of step (a).

5. A process of claim 1 wherein in step (a) the gamma globulin is dissolved in a solution having an ion concentration in the range of 0.010-0.015 mol/l and at a temperature not exceeding 10° C.

6. A process of claim 1 wherein in step (a) the gamma globulin is dissolved in an aqueous solution without added electrolyte and at a temperature of 15-30° C.

7. A process of claim 4 wherein the citrate buffer addition is just prior to the first polyethylene glycol addition and it increases the ion concentration of the solution to 0.06-0.25 ml/l.

8. A process of claim 5 wherein the buffer addition is just prior to the second polyethylene glycol addition.

9. A process of claim 7 wherein the buffer is a 0.03 molar phosphate-citrate buffer.

10. A process for preparing gamma globulin suitable for intravenous administrating comprising
  (a) dissolving 3.0-7.5% by weight Cohn Fraction II powder in a neutral pH aqueous solution containing 0.35-1% by weight hydroxyl ethyl starch;
  (b) separating any precipitate from solution;
  (c) adding polyethylene glycol having a molecular weight of about 4000 to the solution to a concentration of 4.0-5.0%;
  (d) separating the precipitate from the solution, then adding a 5-50 mmol/l citrate phosphate buffer (pH 7.0±0.1) to the solution to a concentrate of 0.2-11.0%;
  (e) adding polyethylene glycol having a molecular weight of about 4000 to the solution to a concentration of 9.5-11.0%;
  (f) separating the purified gamma globulin from the solution;
  (g) dissolving the purified gamma globulin in a solution suitable for IV administration.

11. A product suitable for intravenous administration made by the process of claim 1.

12. A product for intravenous administration made by the process of claim 9.

* * * * *